US011452288B1

(12) United States Patent
Brady et al.

(10) Patent No.: US 11,452,288 B1
(45) Date of Patent: Sep. 27, 2022

(54) INNOCUOUS STERILANT USING HEMOCYANIN AND FUNCTIONALIZED FULLERENES WITH BROAD-SPECTRUM INTRACELLULAR AND INTERSTITIAL MICROBIOCIDAL AND RADICAL SCAVENGING EFFECTS FOR PACKAGED MATTER, BIOLOGICS AND ORGANICS INCLUDING LIQUIDS, GASES, TISSUE, ORGANS, CELLS, AND LIMBS WITH COPPER MEDIATED OXYGENATION FOR VIABILITY AND PRESERVATION

(71) Applicants: Terry Earl Brady, The Valley (AI); Anthony Lee Dellinger, Brown Summit, NC (US); Melinda K. M. Goddard, The Valley (AI)

(72) Inventors: Terry Earl Brady, The Valley (AI); Anthony Lee Dellinger, Brown Summit, NC (US); Melinda K. M. Goddard, The Valley (AI)

( * ) Notice: Subject to any disclaimer, the term of this patent is extended or adjusted under 35 U.S.C. 154(b) by 0 days.

(21) Appl. No.: 17/689,062

(22) Filed: Mar. 8, 2022

(51) Int. Cl.
*A61K 33/00* (2006.01)
*A01N 1/02* (2006.01)
*A61L 2/18* (2006.01)

(52) U.S. Cl.
CPC .............. *A01N 1/0215* (2013.01); *A61L 2/18* (2013.01)

(58) Field of Classification Search
CPC .................................................... A61K 31/00
See application file for complete search history.

(56) References Cited

U.S. PATENT DOCUMENTS

| 9,585,984 B2 | 3/2017 | Wang |
| 9,861,095 B2 | 1/2018 | Dutheil |
| (Continued) | | |

OTHER PUBLICATIONS

Hamblin, "Fullerenes as photosensitizers in photodynamic therapy: pros and cons," Photochem Photobiol Sci 17(11):1515-1533, 2018.*

*Primary Examiner* — Rosanne Kosson

(57) ABSTRACT

Tissue and organ transplantation success is chiefly dependent on the harvest and preservation techniques employed. Yield and quality enhancements are needed, because qualified patient demand far outpaces donors and ultimately, tissues and organs stored and transported so as to render them in acceptable condition for surgery. In the case of corneal transplants, tissue supplies help 1 out of 70 patients in need despite being among the most successful such procedures today. Transplant success has improved overall with enhanced storage and transport methods that have allowed for greater time and distances to reach patients in need, whether corneas, kidneys, hearts, lungs, livers or other tissues, limbs or cellular materials. While corneal tissues specifically benefit from oxygenation via direct air contact and normal tears in a healthy individual, once donated, the lack of corneal vascularization can uniquely accelerate the depletion of oxygen that occurs upon harvesting of all transplant materials. Directly infusing oxygen has had little impact, given partial pressure requirements, volatility and reactivity to many compounds, including self-affinity or agglomeration and bubbling. However, the hemocyanin, such as that of the horseshoe crab (*Limulus polyphemus*), can deliver oxygen directly to transplant tissues, while free radical scavenging by pristine fullerenes can help maintain cellular integrity. Horseshoe crabs have successfully evolved by developing two immunological mechanisms, amoebocytes and less characterized antiviral and gram- (Continued)

positive bactericidal properties ascribed to other hemolymph constituents. The amoebocytes have a specific, ultrasensitive affinity to gram-negative bacteria and fungi; they engulf and consume these microbes in an enzymatic coagulation process. However, hemocyanin is extracellular and non-toxic to mammalian tissue, notwithstanding its microbiocidal properties. As such, the viral-scale peptides appear to intracellularly invade the pathogens and disrupt replication without conferring a caustic or toxic effect on non-pathogenic tissue. Hence, hemocyanin appears to be non-immunogenic and thus applicable as a carrier molecule for some human therapeutics (e.g., hemocyanin from Keyhole Limpet snails). The present invention relates in the initial embodiment to the use of horseshoe crab hemocyanin and functionalized carbon nanostructures, halogenated fullerenes, pristine fullerenes and fullerene derivatives as an antimicrobial and antioxidant enrichment composition that is added to tissue storage and preservation media as a potent, broad-spectrum antimicrobial and tissue preservation composition for safe and effective storage and transport. Notably, methods for horseshoe crab aquaculture husbandry have been developed to achieve sustainable hemocyanin supplies for hemolymph harvest and biomedical applications. With regard to unique needs and benefits for the transplantation of corneal tissue, the aim of this patent is development of an antioxidant and broad-spectrum microbicidal that is benign to endothelial and endothelium cells to preserve and maximize the viability of a pathogen-free specimen.

20 Claims, 1 Drawing Sheet

(56) References Cited

U.S. PATENT DOCUMENTS

| | | |
|---|---|---|
| 11,213,026 B2 | 1/2022 | Lopez |
| 11,224,218 B2 | 1/2022 | Rousselot |

* cited by examiner

INNOCUOUS STERILANT USING HEMOCYANIN AND FUNCTIONALIZED FULLERENES WITH BROAD-SPECTRUM INTRACELLULAR AND INTERSTITIAL MICROBIOCIDAL AND RADICAL SCAVENGING EFFECTS FOR PACKAGED MATTER, BIOLOGICS AND ORGANICS INCLUDING LIQUIDS, GASES, TISSUE, ORGANS, CELLS, AND LIMBS WITH COPPER MEDIATED OXYGENATION FOR VIABILITY AND PRESERVATION

CROSS REFERENCE TO RELATED APPLICATION(S)

N/A.

BACKGROUND OF THE INVENTION

Field of the Invention

This invention relates to a transplant tissue and organ suspension comprised of halogenated and functionalized fullerenes with enhanced relaxivity and hemocyanin to augment the quality, integrity, preservation and sterility of the packaged matter, the storage media, and/or nutrient media. Hemocyanin is found and may be sourced from various Arthropod and Mollusca species, such as the horseshoe crab (*Limulus polyphemus*). The enhancing suspension imparts oxygen transport, broad-spectrum antimicrobial, and free radical scavenging characteristics to traditional storage media and nutrient media, as well as the packaged matter, without the use of potentially harmful biocidal agents such as antiseptics, detergents, disinfectants, antibiotics, antifungals, surfactants, germicides, or immunogenic substances which can lead to cytotoxicity when added to transplanted tissue.

Description of Related Art

This patent follows the U.S. Pat. No. 10,934,168, which describes a synthetic, halogenated, functionalized fullerene (halo fullerene) engineered for biocidal effect. The halo fullerene is physically and caustically destructive to microbial organisms but neutral with respect to larger mammalian cells and tissues. The halo fullerene of U.S. Pat. No. 10,934,168 can be applied to barrier garments, accessory garments (including, but not limited to shoe covers, masks, and facial visors), textiles (including, but not limited to bed sheets, blankets, towels, personal clothing, gowns, surgical drapes, curtains, and pads), filtration matrices (e.g., for use in hemodialysis and hemofiltration), or an aerosolized solution, spray, liquid, salve, or cream. In U.S. Pat. No. 10,934,168, impregnation of the halo fullerenes into an article establishes a resilient and enduring bioactive coating with antimicrobial properties that inhibits growth and proliferation of microbes by rupturing their cellular membranes.

This patent application illustrates yet another embodiment of the invention in the form of a tissue and organ preservation-enhancing suspension that includes halo fullerenes, functionalized fullerenes for enhanced relaxivity and hemocyanin, in this instance, derived from horseshoe crab (*Limulus polyphemus*) hemolymph. In the preferred embodiment, the formulation combines fullerenes with hemocyanin as an enhancing suspension with broad-spectrum antimicrobial, free radical scavenging and oxygen transport capabilities that can be added to or formulated with existing nutrient and preservation media commonly used for organ and tissue transplant storage after harvesting and prior to transplantation. The enhancing suspension may also be used alone as a safe additive for packaged materials, such as biologics, especially in the case where the inclusion of a nutrient source or media is not required for prolonged material preservation.

Global interest in functional materials with broad-spectrum antimicrobial activity has intensified during the SARS-CoV 2 pandemic that began in 2020. While early nanomaterial innovations were often employed as structural enhancements to general consumer products, the transformative potential of nanoparticles has been increasingly applied in pharmaceutical, device, and biotechnology industries. Antimicrobial agents are compounds that inhibit the growth of and/or kill microorganisms, which are globally ubiquitous. Bass Becking most famously hypothesized that "everything is everywhere but the environment selects" (De Wit and Bouvier, 2006). In some respects, this ubiquity is key to human survival, as humans live synergistically with a myriad of microorganisms. Nonetheless, of growing concern and imparted by mutation and adaptation is the increased prevalence of antimicrobial resistance (AMR) of pathogens that has rendered many antibiotics ineffective, with the future appearing more dire as the incidence of therapeutic failures continues to increase (Jindal et al., 2015). As such, robust, scalable, and manufacturable nanomaterials that possess broad-spectrum microbiocidal mechanisms and biocompatibility are urgently needed inventions. In turn, the antioxidative properties demonstrated by functionalized fullerenes have been shown to clear cellular debris so as to maximize cellular integrity and viability via the reduction of reactive oxygen species (ROS). Oxidative stress (induced by ROS) is a major factor that can impact transplantation outcomes. Transplant tissue is prone to oxidative stress injury that may occur pre- and post-transplant. Chiefly, ROS-mediated reperfusion injury triggers initiation of alloimmunity, which is an immune response to non-self antigens from the same species. In turn, this may lead to activation of the transplant recipient's immune system; whereby, cells involved in innate immunity are unable to distinguish between intrinsic ROS-induced stress proteins created by microorganisms or structurally similar human stress proteins that arise during allografts.

Fullerenes are spherical, novel allotropes of carbon that are currently being employed globally in various sectors (Dellinger et al., 2013). These molecules possess electronic properties that make them uniquely suitable for medical applications (Dellinger et al., 2013). Fullerenes also render high antioxidant capacity at extremely small sizes with substantial surface area that can be further functionalized or engineered to provide the framework for next-generation nanomaterial inventions (Dellinger et al., 2013).

Secondary to significant nanomaterial developments, an increased understanding of bioinspired or biologically derived marine molecules has resulted in important contributions to clinical medicine (Santos et al., 2020; Zanjani et al., 2018). The chemical biodiversity of marine organisms has also inspired entries into the pharmaceutical pipelines with 13 marine-derived drugs approved by the United States Food and Drug Administration (FDA) as of 2020 and many more in clinical trials (Jekielek et al., 2021). For some 3.7 billion years, aquatic fauna have existed, which is threefold longer than terrestrial evolution, resulting in far greater diversity (Blasiak et al., 2020). Likewise, microbes predate all other life forms, and the survival and evolution of marine organisms, such as the horseshoe crab, presumes an unmatched innate immunity with microbiocidal properties as evidenced by its continued endurance over countless millennia. Of note and related to this patent application, a component derived from the hemolymph cells, or amebocytes, from the *L. polyphemus* (one of four extant species of horseshoe crabs) is used in the Bacterial Endotoxin Test (BET) for sterility testing of all injectable drugs and implantable devices, and thereby safeguards the biomedical industry and millions of patients who depend on it every year (Tinker-Kulberg et al., 2021). As such, the *Limulus* amebocyte lysate (LAL) assay was approved in 1983 by the FDA for pharmaceutical quality control testing and became the BET of choice for detection of gram-negative bacteria due to its simplicity, specificity, and sensitivity (Hochstein, 1990; Cooper, 2001).

Over 450 million years of horseshoe crab evolution has clearly benefited from two immunological mechanisms: (1) circulating amoebocytes; and (2) less characterized antimicrobial (antiviral, antifungal and bactericidal) properties ascribed to molecules in the Arthropoda hemolymph (Krisfalusi-Gannon et al., 2018). The amebocytes have a specific affinity to gram-negative bacteria and fungi that results in destruction and absorption of the microbes in an enzymatic coagulation process (Tinker-Kulberg et al., 2021). Notably, horseshoe crab peptides have been shown to intracellularly invade host cells containing pathogens and disrupt microbial replication without a caustic or toxic effect to the surrounding host cells (Amiss et al., 2021).

The horseshoe crab breathes through a set of gills and transports oxygen via hemocyanin (Towle and Henry, 2003). Unlike mammalian blood, the hemolymph of horseshoe crabs and other invertebrates does not contain iron but rather copper groups that transport and reversibly bind oxygen via an efficient soluble mechanism with enhanced theoretical efficiency. Similar to vertebrate hemoglobin, horseshoe crab hemocyanin binds oxygen, with each polypeptide subunit capable of binding one molecule of oxygen (Marengo-Rowe, 2006). Unlike vertebrate red blood cell hemoglobin, which is made up of four polypeptides, extracellular horseshoe crab hemocyanin has 48 subunits arranged as eight hexamers [also 1×6mers or oligohexamers (n×6mers) that form the native 8×6mer *Limulus* hemocyanin] (Martin et al., 2007). Accordingly, a single horseshoe crab hemocyanin polypeptide has a binding potential of 48 molecules of oxygen, 12 times the capacity of vertebrate hemoglobin (Brouwer et al., 1977; Van Holde & Miller, 1995). In fact, hemocyanin sustains the horseshoe crab during periods of hypoxia and in response to natural behaviors; whereby, the arthropod may survive outside of the ocean for several days (i.e., evidenced by biomedical bleeding for LAL) or while egg laying and fertilization on shorelines or burrowed in mud (Kobayashi et al., 1995). Similar phenomena have been observed in the hemocyanin of other marine species, such as lobsters. Recent oxygen transfer advancements with human biocompatibility have also included the use of hemoglobin from the polychaete lugworm (*Arenicola marina*), which has similar oxygen affinity to that of horseshoe crab hemocyanin and is also dissolved in the blood (i.e., not contained within red blood cells) with extracellular oxygen transport capabilities (Rousselot et al., 2006). Further, hemocyanin appears relatively non-immunogenic and has been used as a carrier for human therapeutics (e.g., Keyhole Limpet hemocyanin has served as a promising adjuvant in tumor treatment; McFadden et al., 2003).

Despite the evolutionary success of the diverse immunological components (i.e. clotting factors, protease inhibitors, lectins, antimicrobial peptides and other humoral factors) in horseshoe crab hemolymph, their application to marine pharmacognosy has been relatively limited. This has been ascribed in part to raw material supply considerations, given demands on the species for biomedical sterility testing and use as a fishing bait. However, recent developments in aquaculture have suggested greater potential for sustainably adapting unique hemolymph properties into emerging medical applications (Tinker-Kulberg et al., 2021).

The present invention relates to a suspension of hemocyanin and functionalized carbon nanostructures, including halo fullerenes, directed for use as an antimicrobial and antioxidative additive for tissue storage media to enhance preservation and increase surgical opportunities for solid tissue transplantation, with particular and immediate application for corneal replacements, which are among the most frequent and reliably successful transplant procedures (Niederkorn and Ligocki, 2016). As the procedure initially gained acceptance, recipients typically awaited phone calls and then reported for emergency ophthalmic surgery (Chu, 2000). Since 1961, more than 2.1 million corneal transplants have been performed while leveraging efficiencies and advancements in storage techniques, specular microscopy, and improved communication and transportation capabilities between American eye banks (Eye Bank Association of America, 2020). Notably, corneal tissue has subsequently been shown to maintain surgical viability for 11 to 14 days; whereas organs such as, hearts and lungs are limited to 4 to 6 hours; liver, up to 12 hours; and kidneys have been successfully stored as long as 36 hours (Lass et al., 2017). Annually, it is estimated that 185,000 corneal transplants are performed worldwide, with more than 66,000 performed in the United States; while some 55% of all corneas are procured in the United States and India (Gain et al., 2016). However, as with most transplanted organs and tissues, demand far outpaces available donations; whereby, innovations to maximize viability for full utilization through extended transport and storage stability could both improve quality of life and save additional lives. Specifically, an estimated 12.7 million people were recently waiting for corneal transplants, while available supplies were addressing just 1 of every 70 patients, worldwide (Gina et al., 2016).

Such innovation may be particularly beneficial with respect to corneal transplants due to unique characteristics of these tissues. The cornea is comprised of a protective outer layer (epithelium), the stroma, and the inner layer (endothelium). The epithelium is a thin multicellular layer of fast-growing and easily regenerated cells (Dória Silva et al., 2011). The stroma makes up 90% of the corneal thickness, consisting of approximately 200 layers of arranged collagen fibers and keratocytes (Ali et al., 2017). Lastly, the endothelium is monolayer of mitochondria-rich cells that regulate fluid and solute exchange between the aqueous humor and stroma (Smedowski et al., 2015). Unlike the epithelial layer, the cells of the endothelium do not regenerate; however, they are capable of distending or elongating to counterbalance dead cells. These stretching characteristics lower overall cellular density and impact fluid regulation (Bartakova et al., 2014). If they are compromised to the extent that endothelial cells can no longer successfully regulate and maintain proper fluid balance, swelling due to excess fluids and corneal transparency can be affected.

As corneal transplants depend primarily on a viable endothelium, the main cause of graft failure, as well as specimen rejection, has notably related to endothelial decomposition, which is the loss of endothelial cell density or viability, rather than postoperative endothelial cell loss (Nishimura, J. K., 1996; Lass et al., 2010). US surgeons have reportedly demonstrated a preference for corneas that have been stored for no more than 7 days to ensure endothelial cell viability and prevent postoperative graft failures. However, the FDA has approved use of solutions to preserve donated corneas for up to 14 days before transplantation (NIH, 2017). Research has shown that long-term success of corneal transplants remains high even after 11 to 14 days of preservation and storage (Lass et al., 2017).

The first methods of cornea preservation were developed in the 1970s (Summerlin et al., 1973), with McCarey and Kaufman (M-K) Media allowing 48 hours of storage viability that extended the timeline for successful implantation (McCarey and Kaufman, 1974). Over the years, efforts to optimize the storage and transport continued. Today, Optisol-GS™ (Bausch & Lomb Inc.) is the most used corneal storage medium in the United States. Typically, the nutrient medium includes fetal bovine serum in a physiological buffer solution comprised of proteins, fats, hormones, growth factors, antibiotics, alcohol and trace elements in precise ratios for ensuring cellular viability for up to 14 days. However, the viability of corneal cells can drop by up to 50% if stored beyond 14 days, resulting in donor specimen rejection (Pels et al., 1983 and Ayoubi et al., 1996).

The incidence of microbial infections during a corneal transplant procedure can nonetheless have devastating effects upon patient outcomes. In the early years of corneal transplant surgeries, the most common organisms identified in storage media included *Streptococcus pneumoniae*, *Staphylococcus aureus* (coagulase-positive and negative), *Pseudomonas aeruginosa*, and *Cryptococcus neoformans* (Gandhi et al., 1981; Mascarella et al., 1979; Stenson et al., 1980). Since 1991, the Eye Banking Association of America has collected information on positive cultures and identified the most common offending organisms as *Streptococcus/Enterococcus* sp. (46%), fungi (19%), *Staphylococcus* sp. (15%), and Gram-negative rods (7%) (Eye Banking Association of America, 1999).

Most corneal tissue storage and preservation media, like Optisol-GS™, now contain antibiotics, typically gentamicin sulfate and streptomycin sulfate (thus, the "GS" in the media name). The adoption of such antibacterial additives in the 1990s has since played a role in decreasing the incidence of post-surgical bacterial endophthalmitis (Aldave et al., 2013). However, the inclusion of broad-spectrum antibiotics can be harmful to cell viability. Gentamicin sulfate, like other aminoglycosides, imparts an antibacterial mode of action through binding to bacterial ribosomes and inhibiting protein synthesis, employing both bactericidal and bacteriostatic mechanisms. In particular, bactericidal antibiotics have been found to induce both mitochondrial dysfunction and oxidative damage on mammalian cells (Kalghatgi et al., 2013). This is of particular importance to corneal endothelial cells that are mitochondria rich and do not regenerate, as well as problematic to corneal epithelial cells. Similarly, streptomycin sulfate is an aminoglycoside that blocks the ability of 30S ribosomal subunits to make proteins. Notably, aminoglycosides have been shown to induce systemic nephrotoxicity and ototoxicity (Edson and Keys., 1983; Germovsek et al., 2016; Hailey et al, 2017). They have also induced changes in gene expression and chromatin landscape in human cell lines, including genes that are involved in pathways related to insulin response, fatty acid activation, mitochondrial 1-carnitine shuttle pathways, apoptosis, cell growth, and unfolded protein response (Ryu et al., 2017).

While common ophthalmic antibiotics used in drops such as ciprofloxacin, ofloxacin, and moxifloxacin might suggest alternatives to aminoglycosides, they have been found to be incompatible as additives in transplant media even at low concentrations (0.3% to 0.5%) due to rapid antibiotic penetration of the cornea and aqueous humor of enucleated eyes within minutes (Silva et al., 2017). Although the use of antibiotics in ocular drops is well documented and allows for convenient multiuse dropper bottles with increased shelf life and mitigation of microbial contamination, these benefits have not outweighed potential cytotoxicity (Vaede et al., 2010; Baudouin et al., 2010), as a function of concentration and exposure time (Fernández-Ferreiro et al., 2016). As such, these additives could prove especially problematic for corneal tissues, given potential exposure for several days after harvesting and prior to transplantation.

In addition to bacterial contamination, the incidence of fungal infections after corneal transplantation has been increasing in recent years (Aldave et al., 2013). Likewise, these can result in graft rejections, transplant failures, and endophthalmitis (Lin et al, 2016; Chen et al., 2015; Wagoner et al., 2007). Notably, the incidence of postoperative infection-induced inflammation has more than doubled from 2007 to 2014, and fungi (primarily *C. albicans*) was most prevalent (Edelstein et al., 2016), with infections appearing in 7% of the corneas with positive donor rim fungal culture (Mian et al., 2018). Routine fungal treatment strategies require topical corticosteroids to reduce the risk of graft rejection; however, their use can exacerbate an infection during the acute phase (Song et al., 2021). While the addition of antifungal agents to storage media has been proposed (Brothers et al., 2017; Layer et al., 2014), the safety and choice of antifungals has been complicated by risks of endothelial cytotoxicity (Layer et al., 2014), as well as technical limitations, such as colorimetric indicators in the media (phenol red) that cannot reliably detect *C. albicans* contamination (Ritterband et al., 2007). As a result, antifungals are largely absent from transplant media in the US. In Europe, however, transplant media containing antifungals (i.e., Amphotericin B) is more commonplace (Merchant et al., 2001). Ritterband and colleagues (2007), examined voriconazole as an additive to Optisol-GS and found that there was a significant reduction in the rate of positive fungal donor rim cultures with voriconazole-supplemented Optisol-GS, compared with Optisol-GS alone. However, Layer et al. (2014) found significant endothelial toxicity at optimal antifungal concentrations of Amphotericin B in the nutrient media, which is consistent with its adverse effects with both systemic and ocular use (CLSI, Wayne P., 2008).

The SARS-CoV 2 pandemic has likewise complicated transplant efforts with heightened concerns regarding viral particle infiltration of tissue. Given that transplant patients are often immunocompromised and susceptible after surgical procedures, risks from viral particles in transplant specimens have intensified during the pandemic. In one multi-site study, analysis of post-mortem corneal tissue revealed that SARS-CoV 2 was present in conjunctival swabs and tears of 25% of the 132 donors (Sawant et al., 2021). Current intervention techniques have included soaking potentially infected tissue specimens with 5% povidone-iodine for five minutes, followed by a sterile saline fluid flush to eradicate the virus (Mac Rae et al., 1984). As such, only limited exposures to povidone-iodine are feasible, as prolonged incubation negatively effects epithelial and endothelial cells. This factor not only precludes povidone-iodine from acting as a suitable additive for storage media, but it also requires an additional pre-surgical step to ensure virus eradication. Alternatively, other effective antiviral agents that include chlorohexidine, ethanol, and/or other detergents have been eschewed, with numerous reports of exposure causing epithelial defects and corneal edema associated with endothelial disruption (Liu et al., 2016; Oh et al., 2013; Phinney et al., 1988; Tabor et al., 1989).

This patent presents a broad-spectrum microbicidal that is benign to surrounding mammalian cells, including those of the corneal endothelium, combined with restorative oxygen transport molecules, and antioxidant properties, to establish and help preserve a pathogen-free tissue specimen (including viral matter like HIV) for numerous transplant organs, tissues, cellular material, and other clinical applications for which sterility and specimen viability are critical factors.

In Patent Application RU2690153C2 entitled, Method for aseptic prolonged storage and transportation of allogenic implants, donor tissues, using an example of a donor cornea, in a special container with nanomodified surface, Davidovna and Evgenevich teach an aseptic, prolonged storage and transportation container for various viable transplants to increase the period of their storage quality and safe transportation. The container of Davidona and Evgenevich is shaped to conform to the preserved graft material and is made from a nanomodified polymer. The carbon-containing films of Davidona and Evgenvich can be comprised of diamond-like, carbon-containing, fullerene-containing, 0.01-1 mcm thick, with an integral, charged polymer surface. The carbon-containing films are placed into flasks with buffer solution containing silver nanoclusters. The invention of Davidona and Evgenvich prevents deformation of preserved tissues and the risk of biofilm formation or contamination thereof in contact with the biological medium. However, Patent Application RU2690153C2 does not teach the use of a halo fullerene or hemocyanin as antimicrobial agents for prolonged aseptic tissue storage.

In Patent Application JP2006316000A entitled, Preservative for blood or organ and preservation method, Miwa and Matsubayashi teach a new preservative for blood or organ extended storage that suppresses cell damage and possesses excellent stability and handling using fullerenes. The fullerene of Miwa and Matsubayashi includes $C_{60}$, $C_{70}$, a nanotube fullerene, or a mixture thereof. In one example, the fullerene is functionalized with an alkylene side chain, such as a methylene, that is bonded at different positions to the fullerene cage. Side chain attachment groups can be as many as 40 modifying groups in $C_{60}$ and 50 in $C_{70}$ fullerene molecules. Side chain groups are capable of bonding to: a hydroxyl group or an ester group of a hydroxyl group; an inorganic or organic acid or a glycoside group of a sugar; or a ketal group or an aldehyde of a hydroxyl group and a ketone. Additionally, Miwa and Matsubayashi teach that a fullerene product, carbon black, may be used if the concentration of carbon black in the fullerene is 0 to 98% by weight. Miwa and Matsubayashi also teach that a metal-encapsulated fullerene containing, but not limited to, scandium, lanthanum, cesium, and titanium may increase the deodorizing effect of the molecule. However, Patent Application JP2006316000A does not teach the use of a halo fullerene or hemocyanin as antimicrobial agents for prolonged aseptic tissue storage.

In U.S. Pat. No. 9,585,984 B2 entitled, Antibacterial cornea repair material and preparation method thereof, relates to a preparation method of an antibacterial corneal repair material that contains a collagen membrane crosslinked with an antibiotic, preferably tobramycin, gentamicin, ofloxacin or ciprofloxacin. The proposed crosslinked material can repair damaged corneal tissue while reducing the risk of inflammation. However, U.S. Pat. No. 9,585,984 B2 relies on the inclusion of antibiotics as an antibacterial and Wang et al. do not teach the use of a halo fullerene or hemocyanin as antimicrobial agents for prolonged aseptic tissue storage.

U.S. Pat. No. 11,213,026 B2 entitled, Solution for preserving and/or rinsing an organ to be transplanted, describes an aqueous solution for preserving and rinsing organs to be transplanted that is comprised of sodium ions, potassium ions and polyethylene glycol. The solution described in U.S. Pat. No. 11,213,026 B2 aims to reduce cellular alteration and organ disfunction resulting in increased transplant candidates, faster and more efficient graft recovery, and improved transplant organ quality. While polyethylene glycol is a common nanoparticle coating, Lopez does not teach the use of a nanomaterial or hemocyanin as antimicrobial agents for prolonged aseptic tissue storage.

U.S. Pat. No. 11,224,218 B2 entitled, Hemoglobin and uses thereof, relates to an isolated hemoglobin from polychaete worms belonging to the Nereididae family and its use in a cell culture medium and preservation solution as an artificial oxygen carrier for transfusion. The Nereididae hemoglobin is extracellular, dissolved in the blood, and is thus not intracellular. The composition described in U.S. Pat. No. 11,224,218 B2 includes a purified and functional isolate of this hemoglobin at a concentration of at least 0.05 $gL^{-1}$ for use in a cell culture medium. In an alternative embodiment, the polychaete hemoglobin is used to maintain cell viability and metabolic activity in a preservation or maintenance solution that protects organs, tissues, or cells from ischemic reperfusion damage while maintaining the metabolic needs of the organ, tissue, or cell. While U.S. Pat. No. 11,224,218 B2 teaches an oxygen transport molecule of hemoglobin (iron-containing) derived from members of the polychaete worm family Nereididae, Rousselot et al. do not teach copper-binding, extracellular hemocyanin derived from *L. polyphemus* or other Arthropoda or Mollusca, which represent different phyla and species with oxygen transport molecules comprised of distinct subunits and containing copper (not iron, as similar to vertebrate hemoglobin).

U.S. Pat. No. 9,861,095 B2 entitled, Use of extracellular hemoglobin obtained from the marine worm, *Arenicola marina*, for the preservation of organs, tissues, cells, discloses a method for preserving a donor organ comprising an extracellular hemoglobin of Annelida, a stabilizing solution, and/or a solution for conserving organs in temperatures from 4 to 37° C. Medical interest in the lugworm (*A. marina*) dates to 2003, when the outbreak of European bovine spongiform encephalopathy (BSE) and the HIV epidemic had decimated blood supplies. Extracellular hemoglobin from marine polychaetes was considered a potential substitute for animal, human, and generally, vertebrate hemoglobin. Notably, the extracellular nature of the polychaete hemoglobin was determined to be nonimmunogenic, could function over large temperature ranges, passively released oxygen, and possessed a high affinity for oxygen binding. Dutheil et al. teach a composition comprised of at least one extracellular hemoglobin from *A. marina*, as a stabilizing and organ preservation solution with large temperature ranges. Dutheil et al. do not teach extracellular hemocyanin derived from *L. polyphemus* or other Arthropoda or Mollusca, which represent different phyla and species with oxygen transport molecules comprised of distinct subunits and containing copper (not iron, as similar to vertebrate hemoglobin). Further, the inventors do not teach a composition including the addition of fullerene nanoparticles as antimicrobial and free radical scavenging agents, however, Dutheil et al. do teach that extracellular Annelid hemoglobin has inherent copper/zinc-superoxide dismutase (SOD) activity with antioxidant effects, but they do not ascribe any antimicrobial activities to the molecule.

BRIEF SUMMARY OF THE INVENTION

The present invention relates to a composition comprising one or more functionalized and halogenated fullerenes and, in the initial embodiment, horseshoe crab derived hemocyanin, for use as a broad-spectrum antimicrobial, radical scavenging and oxygen transport enhancement solution for transplant storage and nutrient media, as well as other packaged materials. The composition of the present invention can be used for maintaining organ, tissue, and cellular viability with enhanced oxygenation while neutralizing bacterial, viral and fungal pathogens. The effects of the invention would thereby mitigate transplant infectious disease risks while extending the viability of biologics and packaged organic matter, including liquids, gases, tissues, and organs and provide an alternative to conventional preservatives and antimicrobial additives with associated cytotoxicity risks.

The primary object of the present invention leverages the antioxidant and broad-spectrum antimicrobial capabilities and innocuous nature of fullerene nanomaterials, particularly halo fullerenes, and hemocyanin. This invention combines functionalized and halogenated fullerenes with a unique marine antimicrobial substance. The composition is designed to be used to achieve sterility using a benign additive without cytotoxic risks to the material to be stored, packaged, and otherwise preserved. The combination of such fullerenes and horseshoe crab hemocyanin provides redundant antimicrobial and cellular integrity mechanisms, eliminating the need for potentially harmful antibiotics, antifungals, povidone-iodine, chlorohexidine, ethanol, and/or other preservatives or detergents. The present invention is capable of being added to existing nutrient media for tissue preservation or used alone as an enhancing agent to the organic material, e.g., blood or cellular aspirates.

With respect to the formulation, the following active components include, but are not limited to (1) one or more functionalized and halogenated fullerenes and (2) hemocyanin. However, the suspension may incorporate horseshoe crab hemolymph, which includes plasma, hemocyanin, and amebocytes.

The present invention is comprised of active ingredients that are readily available, easily isolated and/or configured and possess broad-spectrum antimicrobial and radical scavenging capabilities in a safe, stable, and effective form.

An important aspect of the invention involves the use of the enhancing solution as an additive to conventional nutrient media, storage solutions or preservation agents, as well as use as a stand-alone antimicrobial, antioxidant and oxygen transport composition.

The present invention provides a composition using functionalized and halogenated fullerenes and hemocyanin for broad-spectrum intracellular and interstitial microbiocidal effects for use as a sterilant or preservation medium for packaged matter, biologics and organics including liquids, gases, tissue, and organs with additional antioxidation and copper-mediated oxygenation characteristics for superior specimen or material viability and longevity. The preservation solution can thus aid in reducing specimen rejection upon transplantation and post-surgical failures due to infection or cellular damage during storage; as well as provide broad-spectrum and benign antimicrobial preservation for use in blood collection specimens, cellular specimens, biologics, and other packaged materials. For descriptive purposes, the concept of a corneal transplant medium additive is used as the exemplary embodiment, but organs (e.g., kidneys, livers, lungs, etc.), tissues (e.g., blood, blood vessels, bones, heart valves, ligaments, skin, tendons, etc.), cells (e.g., stem cells), limbs, or any biological materials are considered compatible with the present disclosure.

DETAILED DESCRIPTION OF THE INVENTION

Figure 1A:
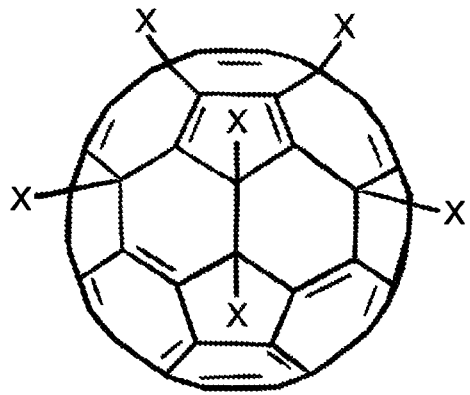
FIGS. 1A, 1B, and 1C are molecular representations of prototypical halo fullerenes of 60 carbon atoms functionalized with 4, 8, or 24 halogens (X).
Figure 1B:
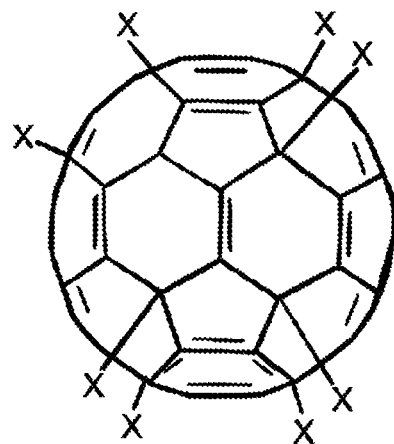
Figure 1C:
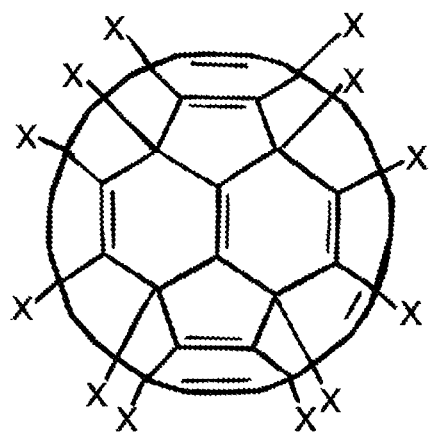

The composition of the present invention includes a novel allotrope of carbon, the fullerenes, which are carbon nanospheres that typically measure less than 100 nm. Fullerenes possess a unique and powerful radical scavenging capability that takes up electrons from radicals (an ongoing organic decay process with microbes). The carbon cage of fullerenes can absorb electrons and disperse them through the 3D π-conjugated structure distributed over its surface. In the present invention, the fullerene cage is vital, because the mass is on the atomic scale (1-100 nm) but arranged in a geodesic configuration of hollow/empty space. The fullerenes draw pathogens toward the carbon nanomaterial orbitals during electron exchanges using atomic forces. These fullerene physical properties represent a stable and broad-spectrum molecule with high binding affinity to all pathogens (which typically possess negatively charged cell walls). Furthermore, the outer carbon cages of the fullerenes are capable of modification via chemical functionalization of side-chain moieties. The use of specific chemical reactions that result in the generation of a halo fullerene, or a functional fullerene cage possessing multiple side-chain halogens (e.g., iodine, bromine, chlorine and fluorine), renders a nano-scale antimicrobial agent. In the present invention, fullerenes are functionalized for aqueous relaxivity as well as bonding with potent halogen molecules to leverage their high pathogen affinity and create an inescapable antimicrobial atomic field. In turn, the halo fullerenes caustically eradicate microbes on contact, without lost energy or halogens, hence maintaining a continuous antimicrobial capability.

A broad range of carbon shell fullerene modifications have been demonstrated via numerous, well-described chemical reactions [Yan, et al., 2015]. The halo fullerene of the present invention is comprised of a fullerene shell of $C_{2n}$; whereby, n=10, 12, 13, 14, 15, . . . 360, such that multiple side-chain halogens can be attached to the core carbon cage. The halo fullerene of the present invention includes three carbon-60 nanomaterials of $C_{60}X_6$; $C_{60}X_8$, and $C_{60}X_{24}$; whereby, X=a halogen molecule (e.g., bromine, chlorine, iodine, or fluorine). In turn, the pristine (non-functionalized) fullerene or functionalized fullerene derivative component includes $C_{60}$, $C_{70}$, $C_{76}$, $C_{78}$, $C_{80}$, $C_{82}$, $C_{84}$ and higher molecular weight molecules with or without the addition of functional groups on the outer shell of the core carbon cage. Functionalized fullerenes include common fullerenol (—OH) nanoparticles, as well as chemical functionalization with amino acids, proteins, peptides, carboxylic acids, polyhydroxyl groups, amphiphilic polymers, or any type of mono- or multi-addition to the external fullerene carbon topology via nucleophilic or pericyclic reactions, hydrogenation, oxidation, hydroxylation, electrophilic, carbene, or radical additions, etc.

Halogen atoms are hydrophobic and lipophilic, which may be exploited for a myriad of applications. Lipophilicity enables halogens to cross and pass through cell membranes. In the parent patent, the halogen functional group applies these highly caustic atomic properties that induce cell rupture and destruction of vulnerable microbes, without a net loss of energy or efficacy, for ongoing caustic capabilities at the application or exposure site. Likewise, pristine fullerenes and functionalized fullerene derivatives have demonstrated iterative capture of free radicals, a dynamic radical scavenging mechanism for maintaining cellular viability, without a net loss of energy or efficacy, for continuous antioxidant capability at the application or exposure site.

In addition to the antioxidative and caustic properties of the functionalized fullerenes in the proposed invention, the composition encompasses hemolymph derived from horseshoe crabs, which contains proteins and peptides associated with its primordial immunity. Among these is hemocyanin, a well characterized molecule found in the Arthropoda, Mollusca, and certain insect hemolymph.

Hemocyanin is a multi-functional protein that provides oxygen transport and host immunity and is the predominant protein component (between 50% to 90%) of invertebrate hemolymph. In *L. polyphemus*, hemocyanins are the largest recorded and present in the highest concentrations, exceeding 100 $mg/mL^{-1}$ (Coates et al., 2017; Coates et al., 2012 and Van Holde et al., 2001). The oxygen binding affinity of horseshoe crab hemocyanin is modulated by protons or various organic ions (e.g., calcium, sodium, chloride, potassium, magnesium, lactate, urate, etc.) with optimal binding at or around physiological pH and across a broad temperature range (4 to 37° C.). Unlike hemoglobin, which is contained in the red blood cells of vertebrates, hemocyanin is dissolved and distributed throughout the hemolymph. While oxygen-transport blood substitutes (i.e., perfluorocarbons, human red blood cells, artificial hemoglobin-based oxygen carriers) require limited, specific conditions, hemocyanin is stable and functional across a broad range of temperatures, including colder environments, which reduce cellular metabolism and are favored in transplant preservation protocols. In contrast to hemoglobin dependence on negative allosteric effectors for oxygen diffusion, *L. polyphemus* hemocyanin can passively release oxygen with a gradient that optimizes uniform delivery without requiring external allosteric interactions.

Given their primary function to transport oxygen to respiring tissues within invertebrates, hemocyanins contain di-cupric groups that reversibly bind molecular oxygen (van Holde et al., 2001) and play a dual role in host immunity. However, *L. polyphemus* hemocyanin notably differs substantially from bulk or nanoscale copper used as a conventional healthcare antimicrobial agent. Likewise, most antibiotics require knowledge of the causative agent for effective application; whereas, this invention utilizes a composition of radical scavenging and antimicrobial halo fullerenes and hemocyanin for antioxidant and broad-spectrum biocidal capabilities across species, as well as mutated species.

In addition to oxygen transport, hemocyanin is associated with numerous homeostatic and physiological processes, such as molting, hormone transport, osmoregulation, and protein storage (Adachi et al., 2005; Kuballa and Elizur, 2008; Glazer et al., 2013; Jaenicke et al., 1999; Paul and Pirow, 1998). Immunologically, hemocyanin is capable of converting into phenoloxidase-like (PO) enzymes upon physical disruption of the structural motifs surround the central coppers. These POs play vital roles in a broad-based response to pathogens (Coates et al., 2012); whereas, hemocyanin demonstrates greater activity than POs against bacteria and fungi. In addition to hemocyanin, horseshoe crab hemolymph contains a range of molecules with profound antimicrobial functionality (Iwanaga, 2002). See Table 1 (Iwanaga, 2002).

TABLE 1

Defense Molecules Found in Amebocytes and Hemolymph Plasma of the Horseshoe Crab.

| Proteins and Peptides | Mass (kDa) | Function Specificity | Localization |
|---|---|---|---|
| | | Coagulation Factors | |
| Factor C | 123 | Serine protease | L-granule |
| Factor B | 64 | Serine protease | L-granule |
| Factor G | 110 | Serine protease | L-granule |
| Proclotting enzyme | 54 | Serine protease | L-granule |
| Coagulogen | 20 | Gelation | L-granule |
| | | Protease Inhibitors | |
| LICI-1 | 48 | Serpin/Factor C | L-granule |
| LICI-2 | 42 | Serpin/Clotting Enzyme | L-granule |
| LICI-3 | 53 | Serpin/Factor G | L-granule |
| Trypsin Inhibitor | 6.8 | Kunitz Type | Not Determined |
| LTI | 16 | New Type | Not Determined |
| LEBP-PI | 12 | New Type | L-granule |
| Limulus Cystatin | 12.6 | Cystatin Family 2 | L-granule |
| a2-Macroglobulin Granule | 180 | Complement | Plasma and L-granule |
| Chymotrypsin Inhibitor | 10 | Not Determined | Plasma |
| | | Antimicrobial Substances | |
| Anti-LPS Factor | 12 | Gram Neg Bacteria | L-granule |
| Tachyplesins | 2.3 | Gram Neg/Gram Pos/Fungal | S-granule |
| Polyphemusins | 2.3 | Gram Neg/Gram Pos/Fungal | S-granule |
| Big Defensin | 8.6 | Gram Neg/Gram Pos/Fungal | L-granule and S-granule |
| Tachycitin | 8.3 | Gram Neg/Gram Pos/Fungal | S-granule |
| Tachystatins | 6.5 | Gram Neg/Gram Pos/Fungal | S-granule |
| Factor D | 42 | Gram Neg Bacteria | L-granule |

TABLE 1-continued Defense Molecules Found in Amebocytes and Hemolymph Plasma of the Horseshoe Crab.

| Proteins and Peptides | Mass (kDa) | Function Specificity | Localization |
|---|---|---|---|
| Lectins | | | |
| TL-1 | 27 | LPS (KDO), LTA | L-granule |
| TL-2 | 27 | GlcNAc, LTA | L-granule |
| TL-3 | 15 | LPS (O-antigen) | L-granule |
| TL-4 | 470 | LPS (O-antigen), LTA | Not Determined |
| TL-5 | 380-440 | N-acetyl Group | Plasma |
| Limunectin | 54 | PC | L-granule |
| 18K-LAF | 18 | Hemocyte Aggregation | L-granule |
| Limulin | 300 | HLA/PC, PE, SA, KDO | Plasma |
| LCRP | 300 | PC, PE | Plasma |
| tCRP-1 | 300 | PE | Plasma |
| tCRP-2 | 330 | HLA/PE, SA | Plasma |
| tCRP-3 | 340 | HLA/SA, KDO | Plasma |
| Polyphemin | Not Det. | LTA, GlcNAc | Plasma |
| TTA | Not Det. | SA, GlcNAc, GalNAc | Plasma |
| Liphemin | 400-500 | SA | Hemolymph |
| Carcinoscorpin | 420 | SA, KDO | Hemolymph |
| GBP | 40 | Gal | Hemolymph |
| PAP | 40 | Protein A | Hemolymph |
| Others | | | |
| Transglutaminase | 8.6 | Crosslinking | Cytosol |
| 8.6 kDa Protein | 8.6 | TGase Substrate | L-granule |
| Pro-rich Protein | 80 | TGase Substrate | L-granule |
| Limulus Kexin | 70 | Precursor Processing | Not Determined |
| Hemocyanin | 3,600 | Oxygen Transporter (PO Activity) | Plasma |
| Toll-like Receptor (tToll) | 110 | Not Determined | Hemocyte |
| L1 | 11 | Unknown | L-granule |
| L4 | 11 | Unknown | L-granule |

Gal: Galactose; GalNAc: N-Acetylgalactosamine; GBP: Galactose-binding Protein; GlcNAc: N-Acetylglucosamine; HLA: Hemolytic Activity; KDO: 3-deoxy-α-D-mannooctulosonic Acid; LAF: Limulus 18-kDa Agglutination-aggregation Factor; LCRP: Limulus C-reactive Protein; LEBP-PI: Limulus Endotoxin-binding Protein-Protease Inhibitor; L-granule: Large Granule; LICI: Limulus Intracellular Coagulation Inhibitor; LPS: Lipopolysaccharide; LTA: Lipoteichoic Acid; LTI: Limulus Trypsin Inhibitor; PAP: Protein A Binding Protein; PC: Phosphorylcholine; PE: Phosphorylethanolamine; PO: Phenoloxidase; SA: Sialic Acid; S-granule: Small Granule; TGase: Protein-glutamine γ-glutamyl-transferase; TL: Tachylectin; TTA: T. Tridentatus Agglutinin.

The cellular material, or the amebocytes, in horseshoe crab hemolymph contains antimicrobial polypeptides and peptides stored in two granules, the small granule (S-granule) and the large granule (L-granule). The S-granule-derived antimicrobial peptides bind to chitin but not to other polysaccharides, such as cellulose, mannan, xylan, and laminarin (Iwanaga, 2002). Both the L- and S-granules contain a substance termed "Big Defensin" that is similar to mammalian neutrophil-derived defensins, but distinct in size (Lehrer, 1992; Ganz and Lehrer, 1995). Big Defensin strongly inhibits the growth of gram-negative and gram-positive bacteria, and fungi (including the cause of most corneal transplant fungal infections, C. albicans). Numerous lectins in both the plasma and granules, and several bacterial agglutinins, interact to protect horseshoe crabs from invading microbes and foreign substances (Iwanaga et al., 1998; Kawabata et al., 2003). Additionally, the hemolymph contains a class of C-reactive proteins (CRP) that exhibits cytolytic and opsonic activities against foreign cells and bears structural similarity to the complement system in mammals (Iwaki et al., 1999).

The antimicrobial polypeptides and peptides of the horseshoe crab hemolymph also demonstrate peptide-membrane interactions and cellular uptake that provide an intracellular bulwark against bacteria, viruses or other pathogens that evade the extracellular environment and may act as latent reservoirs of infection harbored within the cell. Additionally, these peptides are capable of binding to cell receptors and prevent pathogen entry, as well as inhibiting cell-to-cell pathogen proliferation.

The invention suspension is easily added to the packaged material alone or can be used in conjunction with nutrient dense media commonly used for the specific packaged biologics, whether organs or other organic material.

The preferred embodiment of this invention includes caustic halo fullerenes (halogenated functionalized fullerenes), pristine fullerenes and/or a functionalized fullerene derivative, and horseshoe crab hemocyanin in a neutral, buffered, aqueous stabilizing suspension for use as an additive to media or as a standalone antimicrobial composition for package materials that require sterility. The extracellular hemocyanin is contained in the hemolymph collected from the horseshoe crab (or alternative Arthropoda or Mollusca hemocyanin source) and can be purified from the hemolymph. In addition to antimicrobial capabilities, the inclusion of horseshoe crab hemocyanin transports and delivers necessary oxygen. The composition is further understood to be nontoxic, neutral with respect to organic matter and otherwise innocuous to any non-pathogenic components. It is also understood that additional embodiments may include halo fullerenes, other functionalized fullerenes, pristine fullerenes, hemocyanin, and other components contained in hemolymph as a sterilant composition.

The inclusion of halo fullerenes and hemocyanin provides broad protection from pathogens with multiple mechanisms to impede microbial mutation and resistance as alternatives to antibiotic additives. The invention would impart the intended antimicrobial benefits of antibiotics while averting risks of tissue cell wall or plasma membrane damage, disruption of DNA or RNA synthesis, inhibition of protein synthesis through binding of peptides with ribosomal subunits, or interfering with bacterial metabolic pathways. Apart from some broad-spectrum classes, antibiotic efficacy is also typically optimized with known species—but ineffective against viruses and fungi, all of which may be difficult to anticipate in tissue and organ transport or storage. Confounding possibilities also include those of co-colonization between two types of species (i.e., gram-negative and gram-positive bacteria) or across microorganisms (e.g., a fungus, gram-negative bacteria, and virus).

In theory, including broad-spectrum antibiotics in combination with antifungal and antiviral material would represent the most comprehensive approach to ensuring sterile tissue and organ storage and transport. However, optimal concentrations of such additives have been shown to pose risks of cytotoxicity and lost specimen viability. Another consideration is temperature, as antibiotics are generally most effective at higher temperatures than those in typically cooler tissue and organ storage conditions.

The combination of halo fullerenes and more broadly, radical scavenging pristine fullerenes and/or fullerene derivatives, and hemocyanin would establish a comprehensive antimicrobial solution to eradicate bacteria, viruses, or fungi, with a broader range of temperature and storage flexibility than antibiotics and antifungals. Furthermore, replacing traditional preservation additives such as surfactants, antiseptics, detergents, and disinfectants with halo and scavenging fullerenes and hemocyanin would provide sterility while further mitigating risks of cytotoxicity to improve specimen quality and viability, as well as potential longevity from antioxidant activity.

Beyond antimicrobial attributes of the proposed composition, the use of hemocyanin is directed at stabilizing vulnerable organ, tissue, and cellular specimens after harvest. Oxygenation of donor material for a suitable duration that allows for transport and improves specimen storage and preservation are essential to maintaining the quality, prolonged viability, and ultimately, a successful transplantation. Hemocyanin offers functional oxygen transport advantages over use of human red blood cells, hemoglobin-based oxygen carriers, and perfluorocarbons, which rely on specific temperatures, pressurized environments, and allosteric effects to optimize oxygenation. Preferably the composition is delivered in a commercial aqueous stabilizing or preservation solution commonly used for the target transplant material including, but not limited to: BMPS Belzer®; Celsior®; Custodiol®; Euro-Collins®; IGL-1®; Optisol-GS™; Perfadex®; Plegisol®; SCOT 15 Multi Organes Abdominaux®; SCOT 30 Greffons Vasulaires®; Ringer Lactate®; Soltran®; Steen®; and Viaspan® solutions. The inclusion of stabilizing agents in the composition may also comprise organic or inorganic ions, including one or more of the following: calcium, chloride, lactate, magnesium, potassium, sodium, urate, or another divalent ion, at a concentration that enhances hemocyanin and oxygen binding affinities. It is further understood that the composition is suitable as a cold sterilization solution that is a non-corrosive and safe agent for medical instruments. Most commercial cold-sterilant solutions (i.e., Cidex®, Cidex Plus®, Cetylcide-G®, Banicide®) contain the active ingredient glutaraldehyde and have proven effectiveness against viruses, bacteria, fungi and tuberculosis; however, glutaraldehyde has been linked to a variety of maladies (e.g., asthma, breathing difficulties, respiratory irritation, skin rashes, etc.). The composition of the proposed invention would confer optimal sterilization capabilities with reduced hazards compared to such activated glutaraldehyde sterilants.

In addition to use in storage, preservation and transport media, the proposed composition may be directly perfused into or over the donor organ or tissues before, awaiting and throughout the harvest procedure to prevent warm ischemia, and prior to cooling the harvested material. During this time, transplant material can rapidly deteriorate from oxygen and nutrient depletion and consequent necrosis. Mitigation of ischemia-reperfusion injury is key to prolonging viability and specimen integrity for transplant. As such, the solution may be administered with an arterial, venous, or a triple lumen catheter, or an extracorporeal membrane oxygenation (ECMO) system, or a similar technique to provide oxygenation to target organs or tissues.

The invention composition may also be used as a non-staining antiseptic, biocidal, free radical antioxidant, and oxygen transporting topical or washing suspension. Iodine and derivative complexes (i.e., povidone iodine) are traditional medical biocidal disinfectants (Lepelletier et al., 2020). Notably, the use of iodine and the complexed forms with increased stability are known to cause epidermal irritation and staining. While the commercial use of iodine solutions as an antiseptic is well described, the active iodine ingredient concentration must remain low and requires solubilizing agents or carriers to prevent unwanted irritation, cytotoxicity, systemic distribution, tissue/cellular damage, and excessive staining (Flynn, 2003; Fumal, 2002; Balin and Pratt, 2002; Niedner, 1997; Van den Broek et al., 1982; Viljanto, 1980). Like many antiseptics, efficacy and potential risks are largely dependent on concentration; therefore, longer exposure (i.e., up to 36 hours) may be necessary for optimal results (Lawrence 1988a; Lawrence 1998b). The composition of the proposed invention would provide the microbiocidal benefits of iodine and complexed iodine-based antiseptics, while eliminating concentration dependent side effects and staining. It would also impart oxygen transport and free radical scavenging properties that could promote cellular integrity and healing when applied to a wound, such as a burn, ulcer, laceration, surgical site, etc.

Additional embodiments would include obvious combinations of the above-mentioned approaches or complementary molecules to those that have been proposed and as described in the specification of the patent. Particularly, the invention would be relevant to blood banking storage of packed red blood cells and platelets. Red blood cells exist in a variety of shapes, contours, are increasingly "sticky," and dense in both hemoglobin and iron. These cells represent the most abundant cell type in the blood ($4.2$-$6.1 \times 10^9$ cells $mL^{-1}$) and play a role in innate immunity. In circulation, pathogens coexist and are recognized by the white cells as antigenic matter. However, the inventors have observed that gram-negative bacteria, and likely many other pathogens, have evolved to elude the host's immunological response through a red blood cell affinity, which conceals the pathogen from host defenses (likely similar in the case of platelets). Thus, in the case of blood banking, there is a significant risk that pathogenic material can be transferred when bound to red blood cells or platelets. The proposed invention establishes an innocuous sterilant with broad-spectrum antimicrobial properties for banked blood with enhanced cellular integrity that would promise significantly improved quality of donated and stored blood, one of the most common tissue transplants performed as transfusions, worldwide. As such, the various embodiments disclosed in this patent thus provide illustration, not limitations; the intended scope is therefore reflected in the following claims.

What is claimed:

1. An antimicrobial composition that has broad-spectrum biocidal activity to eradicate bacteria, viruses, and fungal pathogens, wherein the antimicrobial composition has oxygen transport activity, maintains the integrity of cells and does not comprise the integrity of packaged materials, the antimicrobial composition comprising:
   a. a biocidally effective amount of one or more halo fullerenes with the chemical formula of $C_{60}X_6$, $C_{60}X_8$, or $C_{60}X_{24}$, wherein X is a halogen selected from the group consisting of fluorine, chlorine, bromine, and iodine;
   b. a biocidally effective amount of one or more pristine fullerenes with the chemical formula of $C_{60}$, $C_{70}$, $C_{76}$, $C_{78}$, $C_{80}$, $C_{82}$, or $C_{84}$;
   c. an effective amount of horseshoe crab or other invertebrate extracellular hemocyanin;
   d. optionally one or more organic or inorganic ions; and
   e. a buffer to maintain neutral pH of the composition.

2. The composition of claim 1, wherein the concentration of halo fullerenes is between 0.01% and 10.0%.

3. The composition of claim 1, wherein the concentration of pristine fullerenes is between 0.01% and 10.0%.

4. The composition of claim 1, wherein the concentration of extracellular hemocyanin is between 1.0 μg/mL and 1,000 μg/mL.

5. The composition of claim 1, which further comprises one or more of the following: raw hemolymph, proteins or peptides from the phylum Arthropoda or Mollusca.

6. The composition of claim 1, which further comprises one or more functionalized fullerene derivatives.

7. The composition of claim 1, wherein the organic or inorganic ions include one or more of the following: calcium, sodium, chloride, potassium, magnesium, lactate, urate, or another divalent ion, at a concentration that enhances hemocyanin and oxygen-binding affinities.

8. The composition of claim 1, wherein the halo fullerenes, pristine fullerenes, and hemocyanin are biocidal and neutralize bacterial, fungal and viral pathogens present in the packaged material.

9. The composition of claim 1, wherein the halo fullerenes, pristine fullerenes, and hemocyanin are antioxidants that scavenge free radicals present in the packaged material.

10. The composition of claim 1, wherein the buffer is sufficient to maintain a neutral or physiological pH during the period of contact.

11. The composition of claim 1, wherein the composition sustains the viability without damage to the packaged material.

12. A method of preserving and maintaining an organ, a tissue, a limb, a cell, a nutrient medium, a storage medium, a packaged material, or reusable instruments or devices, by contacting the organ, the tissue, the limb, the cell, or the other packaged material with a therapeutically effective amount of the composition of claim 1.

13. The method of claim 12, wherein the contacting comprises soaking, immersion, perfusion, flushing, washing, mixing, combining, or diluting.

14. The method of claim 12, wherein the contacting of the organ, tissue, limb, cell, nutrient medium, storage medium, or other packaged material with the composition of claim 1 sterilizes or neutralizes bacterial, viral, and fungal pathogens contained in or on the organ, the tissue, the limb, the cell, nutrient medium, storage medium, or other packaged material.

15. The method of claim 12, wherein the contacting of the organ, tissue, limb, cell, nutrient medium, storage medium, or packaged material with the composition of claim 1 preserves and maintains the integrity the organ, tissue, limb, cell, nutrient medium, storage medium, or packaged material with antioxidant, radical-scavenging properties.

16. The method of claim 12, wherein the organ, the tissue, the limb, cell or other material is intended for transplantation.

17. The method of claim 12, wherein the packaged material is a reusable instrument or device.

18. The method of claim 12, wherein contacting the reusable instruments and the devices with the composition of claim 1 cold sterilizes the reusable instruments and the devices.

19. A method for non-staining disinfection of a substrate with oxygen transport and free-radical scavenging properties, comprising contacting the substrate with an amount of the composition of claim 1 that is effective for disinfection.

20. The method of claim 19, wherein the substrate is skin, ocular regions, organs, tissues, or wounds.

* * * * *